(12) United States Patent
Jean

(10) Patent No.: US 9,724,444 B2
(45) Date of Patent: Aug. 8, 2017

(54) SCENT FRAME AND DISPOSABLE SCENT PAPER BOX

(71) Applicant: Cha-Lin Jean, Taipei (TW)

(72) Inventor: Cha-Lin Jean, Taipei (TW)

(*) Notice: Subject to any disclaimer, the term of this patent is extended or adjusted under 35 U.S.C. 154(b) by 0 days.

(21) Appl. No.: 15/284,654

(22) Filed: Oct. 4, 2016

(65) Prior Publication Data

US 2017/0100502 A1    Apr. 13, 2017

(30) Foreign Application Priority Data

Oct. 13, 2015   (TW) .............................. 104216392 A

(51) Int. Cl.
*A61L 9/012* (2006.01)
*A47G 1/06* (2006.01)

(52) U.S. Cl.
CPC ................ *A61L 9/012* (2013.01); *A47G 1/06* (2013.01); *A61L 2209/13* (2013.01)

(58) Field of Classification Search
CPC ....................................................... A47G 1/06
See application file for complete search history.

(56) References Cited

U.S. PATENT DOCUMENTS

| | | | | |
|---|---|---|---|---|
| 5,253,440 | A * | 10/1993 | Chang ...................... | A47G 1/06 40/748 |
| 5,361,522 | A * | 11/1994 | Green .................. | A47G 1/0616 239/58 |
| 6,694,656 | B2 * | 2/2004 | Flodin .................... | A47G 1/143 40/748 |
| 8,985,479 | B2 * | 3/2015 | Dobler .................... | A61L 9/048 239/289 |
| 2003/0017129 | A1 * | 1/2003 | Maleeny ................ | A01N 25/10 424/76.2 |
| 2003/0200690 | A1 * | 10/2003 | Galloway ............ | A47G 1/0633 40/779 |
| 2003/0204982 | A1 * | 11/2003 | Bloom ................... | A47G 1/142 40/789 |
| 2008/0016743 | A1 * | 1/2008 | Graves ................. | A47G 1/0616 40/768 |
| 2008/0216374 | A1 * | 9/2008 | Ozmun ................ | A47G 1/0605 40/723 |
| 2009/0119965 | A1 * | 5/2009 | Broehl ...................... | A47G 1/06 40/721 |
| 2011/0146125 | A1 * | 6/2011 | Orme-Johnson .... | A47G 1/0616 40/725 |

* cited by examiner

*Primary Examiner* — Gary C Hoge
(74) *Attorney, Agent, or Firm* — McClure, Qualey & Rodack, LLP

(57) ABSTRACT

A scent frame includes a frame body, a rear plate, a transparent plate, a scent layer, and a rear cover. The frame body includes a frame window. The rear plate is on one side of the frame body and fixedly connected to the frame body. The rear plate includes an opening. The transparent plate is in the frame body to shield the frame window. A receiving space is formed between the transparent plate and the opening. The scent layer is in the receiving space and near to one surface of the transparent plate. The rear cover is on the opening of the rear plate to shield the receiving space. The rear cover includes one through hole. Accordingly, fragrance of the scent layer can be spread from the through hole, and the scent frame can be placed on a surface or hung on a wall, based on different needs.

20 Claims, 9 Drawing Sheets

SCENT FRAME AND DISPOSABLE SCENT PAPER BOX

CROSS-REFERENCE TO RELATED APPLICATION

This non-provisional application claims priority under 35 U.S.C. §119(a) to Patent Application No. 104216392 filed in Taiwan, R.O.C. on Oct. 13, 2015, the entire contents of which are hereby incorporated by reference.

BACKGROUND

Technical Field

The instant disclosure relates to a frame, in particular, to a scent frame and a disposable scent paper box having a scent layer therein for spreading fragrance.

Related Art

Frames are widely used in our daily life, and pictures or photos may be received in the frames for ornamental purposes. The frames are usually placed indoors, e.g., on a desk, on a nightstand, or the frames may be hung on the wall. Nevertheless, conventional frames provide ornamental purposes in solely visual aspects.

A conventional frame with fragrance is developed in which a fragrance sheet is externally attached to the support of the frame. The fragrance sheet spreads fragrance. Therefore, when a user watches the picture or the photo in the frame, he or she can also smell the fragrance spread from the fragrance sheet. However, since the fragrance sheet is externally attached to the frame, the beauty of the frame may be reduced. Moreover, the fragrance sheet can provide fragrance in a limited time duration. After the fragrance sheet fails to provide fragrance, the user has to buy a new fragrance sheet or, in some cases, a new frame, both of which cost money.

SUMMARY

In view of these issues, how to provide a frame having beautiful appearance and capable of spreading fragrance for a long period is an issue. One embodiment of the instant disclosure provides a scent frame comprises a frame body, a rear plate, a transparent plate, a scent layer, and a rear cover. The frame body comprises a frame window. The rear plate is on one side of frame body and fixedly connected to the frame body. The rear plate comprises an opening. The transparent plate is in the frame body to shield the frame window. A receiving space is formed between the transparent plate and the opening. The scent layer is in the receiving space and near to one surface of the transparent plate. The rear cover is on the opening of the rear plate to shield the receiving space. The rear cover comprises at least one through hole.

In one embodiment, the rear cover is rotatably connected to a periphery of the opening.

In one embodiment, the scent frame further comprises a bottom layer and a breathable layer. The bottom layer is in the receiving space and between the transparent plate and the scent layer. The breathable layer is a mesh structure and comprises a plurality of breathable holes. The breathable layer is in the receiving space. The bottom layer, the scent layer, and the breathable layer are sequentially stacked with each other.

In one embodiment, the scent frame further comprises a support. One of two ends of the support is fixed on an outer surface of the rear cover, and the other end of the support is connected to the outer surface of the rear cover via a wire.

In one embodiment, the scent frame further comprises a plurality of pressing sheets on an outer surface of the rear plate. The pressing sheets are on at least one side of the rear plate and near to the opening. When the pressing sheets are rotated relative to the rear plate, the pressing sheets are in contact with and positioned with the rear cover.

In one embodiment, a dimension of the at least one through hole is in the range from 0.3 to 0.8 cm.

In one embodiment, the rear cover further comprises at least one hanging member on an outer surface of the rear cover.

In one embodiment, the rear cover further comprises a plurality of cushioning pads on an inner surface of the rear cover.

In one embodiment, a depth is between the frame window and the opening, and the depth is not less than 1 cm.

In one embodiment, the scent layer comprises a woven cloth layer.

In one embodiment, the scent layer comprises a paper-made layer.

In one embodiment, the scent layer comprises a foam layer.

In one embodiment, the scent frame further comprises two bars received in the receiving space, and the scent layer further comprises two protruding portions respectively protruding from two opposite sides of the scent layer. Each of the bars has a cut groove and an assembling hole at a bottom of the cut groove. The cut grooves respectively receive the two opposite sides of the scent layer. Each of the assembling holes is engaged with the corresponding protruding portion.

Another embodiment of the instant disclosure provides a disposable scent paper box comprising a box body, a scent layer, two bars, and a cover. The box body comprises a receiving space, a through hole, and an insertion opening. The through hole and the insertion opening communicate with the receiving space. The scent layer is in the receiving space and partially exposed from the through hole. The scent layer has two protruding portions respectively protruding from two opposite sides of the scent layer. Each of the bars has a cut groove and an assembling hole at a bottom of the cut groove. The cut grooves respectively receive the two opposite sides of the scent layer. Each of the assembling holes is engaged with the corresponding protruding portion. The cover is connected to one side of the box body to shield the insertion opening.

In one embodiment, the box body has a hanging portion for being hung on a wall.

In one embodiment, the disposable scent paper box further comprises an adhesive member for sticking the box body onto a surface or a wall.

Based on the embodiments of the scent frame and the disposable scent paper box, the fragrance from the scent layer can be spread over a room. In addition, the user can choose scent layers with different fragrance for different purposes, e.g., for delighting the user or for expelling parasites. The scent layer can be replaced conveniently or can be refilled with perfumes, fragrant essential oils, or flavorings for repeated use. The scent frame can be placed on a surface or hung on a wall, and the appearance of the scent frame is not changed when the scent layer is added to the scent frame. On the other hand, the disposable scent paper box not only can provide visually ornamental purposes for the user, but also can provide fragrance by the scent layer. The user can place or stick the disposable scent paper box on a surface (e.g., a desk surface or a wall surface).

Detailed description of the characteristics and the advantages of the instant disclosure are shown in the following embodiments. The technical content and the implementation of the instant disclosure should be readily apparent to any person skilled in the art from the detailed description, and the purposes and the advantages of the instant disclosure should be readily understood by any person skilled in the art with reference to content, claims, and drawings in the instant disclosure.

BRIEF DESCRIPTION OF THE DRAWINGS

The disclosure will become more fully understood from the detailed description given herein below for illustration only, and thus not limitative of the disclosure, wherein.

DETAILED DESCRIPTION

Figure 1:
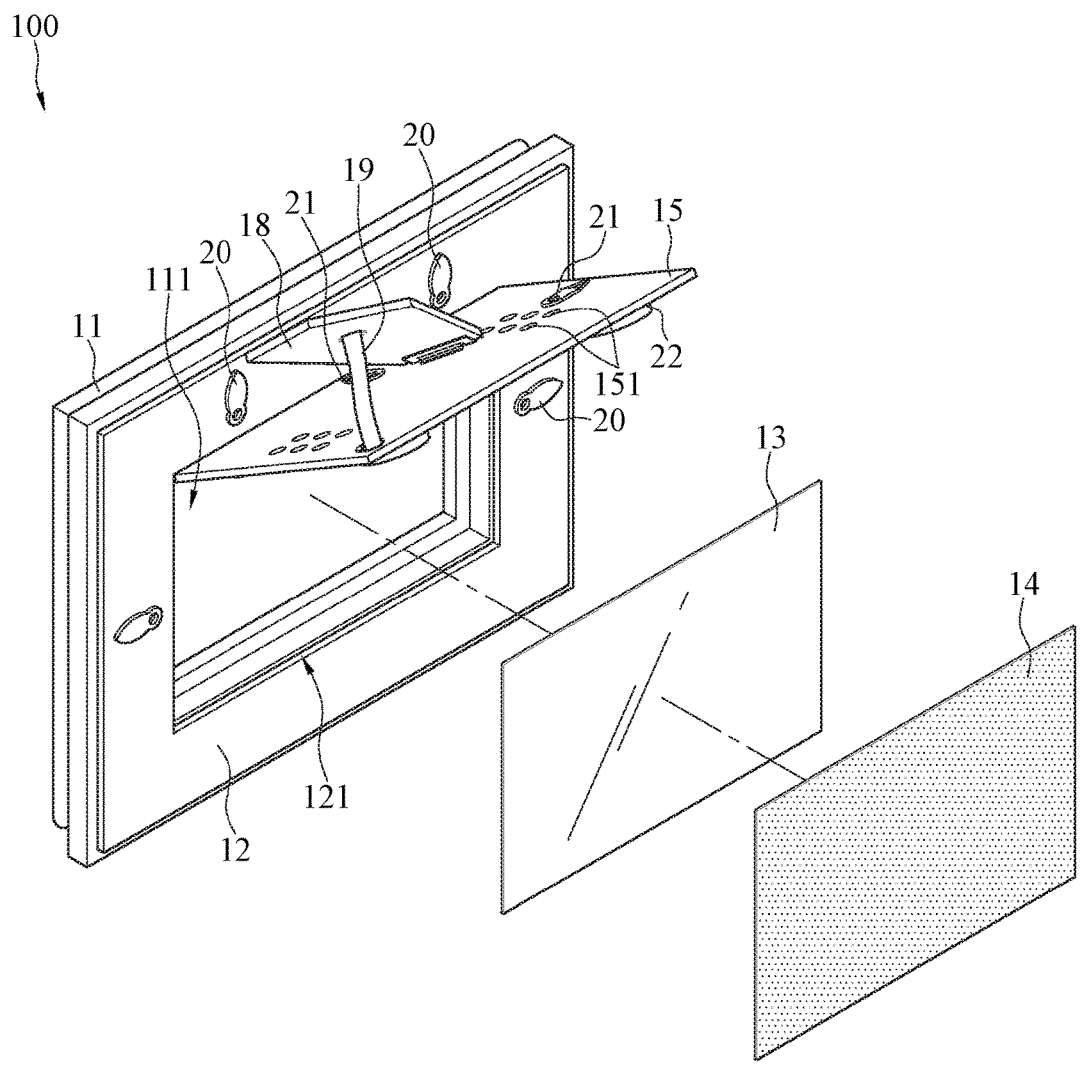
FIG. 1 illustrates an exploded view of a scent frame according to a first embodiment of the instant disclosure.

FIG. 1 illustrates an exploded view of a scent frame 100 according to a first embodiment of the instant disclosure. The scent frame 100 comprises a frame body 11, a rear plate 12, a transparent plate 13, a scent layer 14, and a rear cover 15. The frame body 11 comprises a frame window 111. The rear plate 12 is on one side of the frame body 11 and fixedly connected to the frame body 11. The rear plate 12 comprises an opening 121. The opening 121 may be in communication with the frame window 111.

Figure 4:
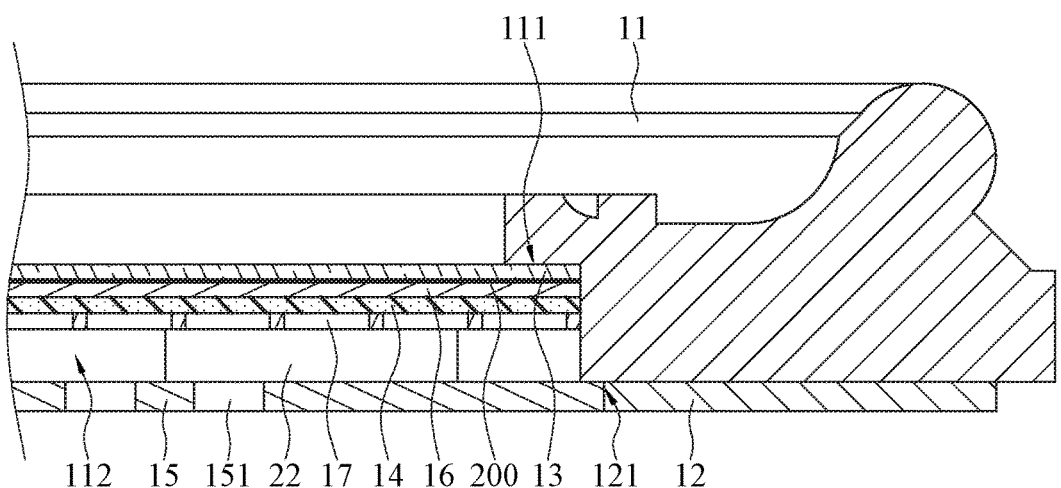
FIG. 4 illustrates a partial sectional view of the scent frame of the third embodiment.

The dimension of the frame window 111 may be smaller than that of the opening 121. The transparent plate 13 is received in the frame body 11 via the opening 121 to close the frame window 111, and a receiving space 112 is formed between the transparent plate 13 and the opening 121 (as shown in FIG. 4). The scent layer 14 is in the receiving space 112 and near to one surface of the transparent plate 13. The rear cover 15 comprises at least one through hole 151. The rear cover 15 is on the opening 121 of the rear plate 12 to shield the receiving space 112. In this embodiment, the rear cover 15 is rotatably connected to a periphery of the opening 121.

Figure 2:
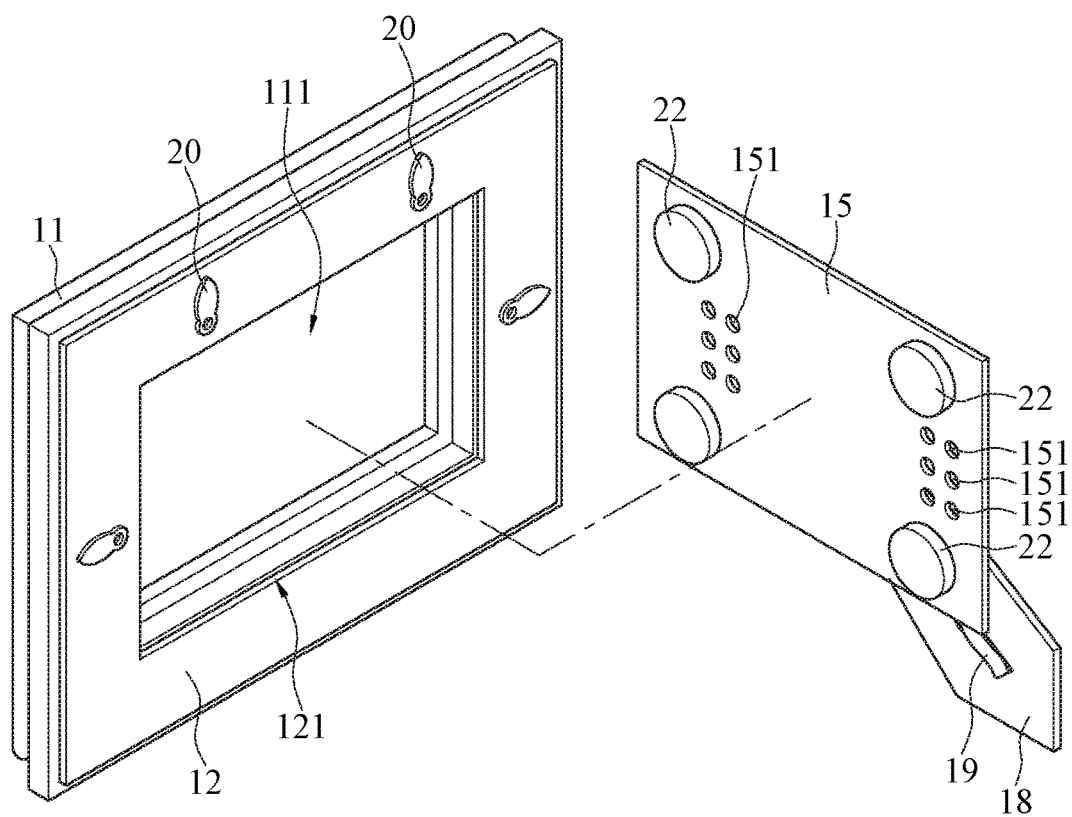
FIG. 2 illustrates an exploded view of a scent frame according to a second embodiment of the instant disclosure.

FIG. 2 illustrates an exploded view of a scent frame 100 according to a second embodiment of the instant disclosure. In this embodiment, the rear cover 15 is not connected to the rear plate 12. The rear cover 15 may be detached off the rear plate 12, or the rear cover 15 may be combined with the rear plate 12 to shield the opening 121.

Figure 3:
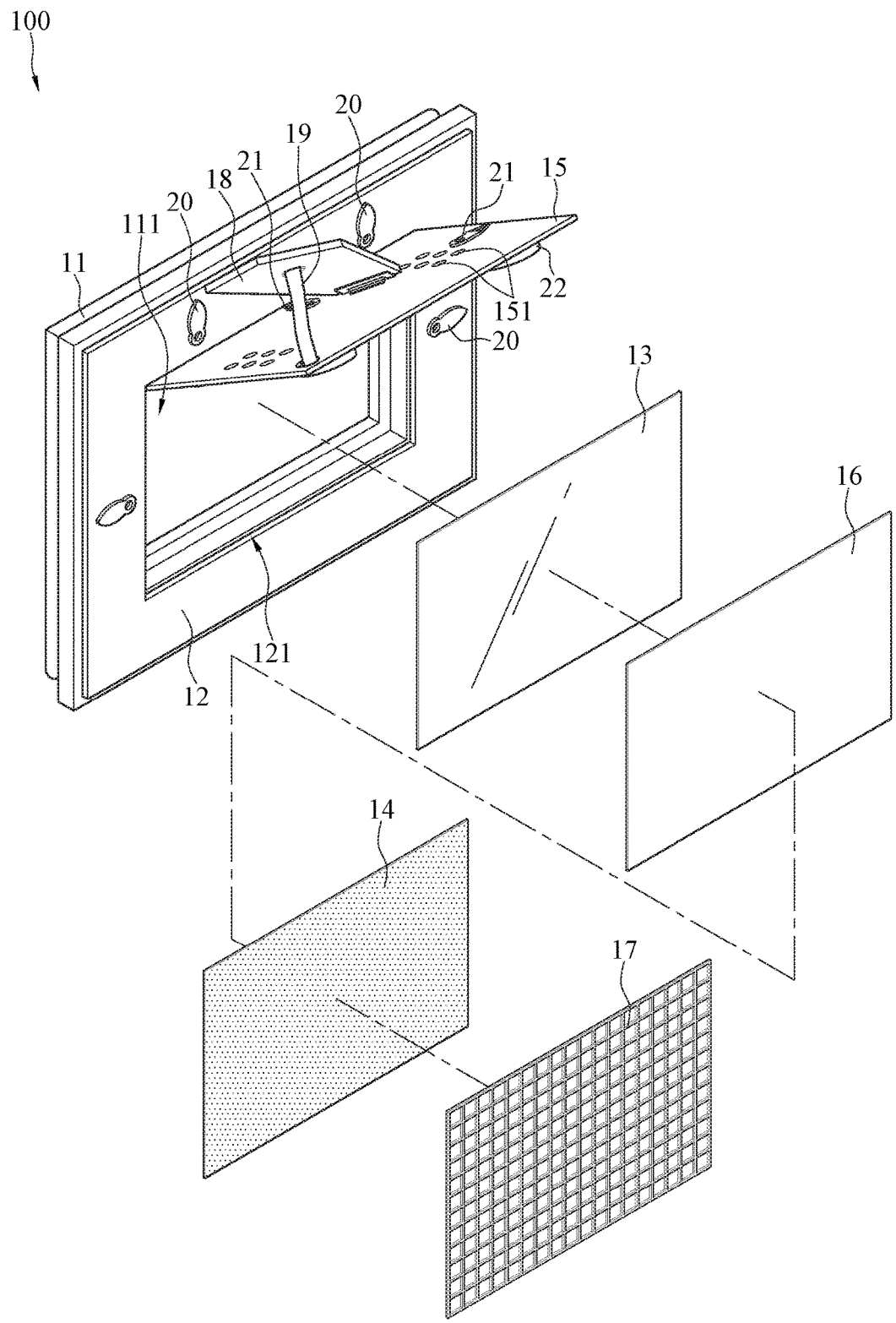
FIG. 3 illustrates an exploded view of a scent frame according to a third embodiment of the instant disclosure.

FIG. 3 illustrates an exploded view of a scent frame 100 according to a third embodiment of the instant disclosure. In this embodiment, the connection between the rear cover 15 and the frame body 11 is similar to that shown in the first embodiment. In this embodiment, the scent frame 100 further comprises a bottom layer 16 and a breathable layer 17. The bottom layer 16 is in the receiving space 112 and between the transparent plate 13 and the scent layer 14. The breathable layer 17 is a mesh structure and comprises a plurality of breathable holes 171. The breathable layer 17 is in the receiving space 112. The bottom layer 16, the scent layer 14, and the breathable layer 17 are sequentially stacked with each other.

In the foregoing embodiments, the photo may be sandwiched between the transparent plate 13 and the scent layer 14 (as shown in the first embodiment), or may be sandwiched between the bottom layer 16 and the transparent plate 13 when the scent layer 14 further comprises the bottom layer 16 and the breathable layer 17 (as shown in the third embodiment). The scent layer 14 provides fragrance. In some embodiments, the scent layer 14 may be a woven cloth layer, a paper-made layer, or a foam layer. In other words, the scent layer 14 may absorb perfumes, fragrant essential oils, or flavorings prior to its reception. Alternatively, the scent layer 14 may be a paper-made layer processed with fragrance. Therefore, the scent layer 14 can be replaced or refilled freely. The fragrance of the scent layer 14 can be spread from the through hole 151 of the rear cover 15. In addition, perfumes, fragrant essential oils, or flavorings may be added to the scent layer 14 by pipettes or syringes through the through hole 151 of the rear cover 15.

The bottom layer 16 is for separating the photo from the scent layer 14. Hence, the photo can be prevented from directly contacting the scent layer 14 and not being contaminated and damaged by the scent layer 14. The bottom layer 16 may be a plastic layer or a metal layer, but embodiments are not limited thereto.

The breathable layer 17, on one hand, can facilitate the fragrance to be volatized and spread slowly. That is, the breathable layer 27 prevents the fragrance of the scent layer 14 from being released from the scent layer 14 rapidly and concentratedly, which may cause the discomfort of the user. On the other hand, the breathable layer 17 can be provided for separating the scent layer 14 from directly contacting the rear cover 15. The separation between the scent layer 14 and the rear cover 15 may prevent the rear cover 15 from being contaminated or damaged easily by the direct contact with chemistries of the perfumes, fragrant essential oils, or flavorings.

Please refer to FIGS. 1 to 3. In the foregoing embodiments, the scent frame 100 may further comprises a plurality of pressing sheets 20 on an outer surface of the rear plate 12. The pressing sheets 20 are on at least one side of the rear plate 12 and near to the opening 121. When the pressing sheets 20 are rotated relative to the rear plate 12, the pressing sheets 20 can be in contact with and positioned with the rear cover 15. Therefore, the rear cover 15 is not easily detached from the frame body 11, and the article(s) in the receiving space 112 would not fall from the receiving space 112. The scent frame 100 may further comprises a support 18, one of two ends of the support 18 is fixed on the outer surface of the rear cover 15, and the other end of the support 18 is connected to the outer surface of the rear cover 15 via a wire 19. Therefore, the user can stand the scent frame 100 on a surface easily. In addition, as shown in FIGS. 1 and 3, the scent frame 100 may further comprise at least one hanging member 21 on the outer surface of the rear cover 15. Accordingly, the user can use either the support 18 or the hanging member 21 to allow the scent frame 100 to stand on a surface or to be hung on a wall.

Please refer to FIGS. 1 to 3. In the foregoing embodiments, the scent frame 100 may further comprise a plurality of cushion pads 22 on an inner surface of the rear cover 15. In the case that the rear cover 15 shields the opening 121 and an external force is applied to the scent frame 100 so that the rear cover 15 is impacted by the articles in the frame body 11 (i.e., the articles in the receiving space 112), the impact force can be partly transferred to the cushion pads 22, and the force applied to the rear cover 15 can be reduced. Conversely, because of the cushion pads 22, the force applied to the articles in the frame body 11 can be reduced as well. Taking the third embodiment as an example, the articles in the frame body 11 are the transparent plate 13, the photo, the bottom layer 16, the scent layer 14, and the breathable layer 17, and the cushion pads 22 can be provided as buffer members between these articles and the rear cover 15.

Figure 5:
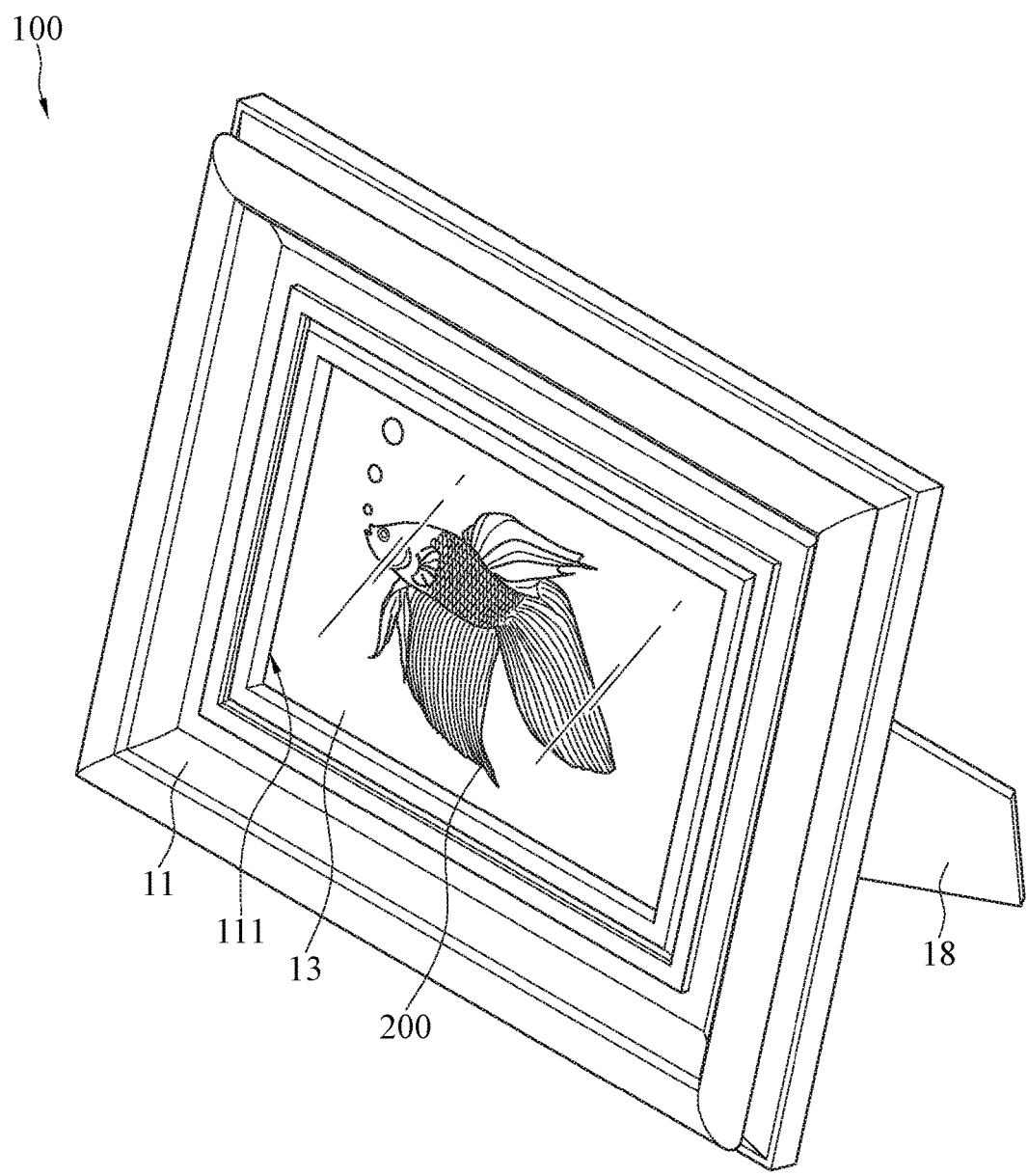
FIG. 5 illustrates a perspective view (1) of the scent frame of the third embodiment.
Figure 6:
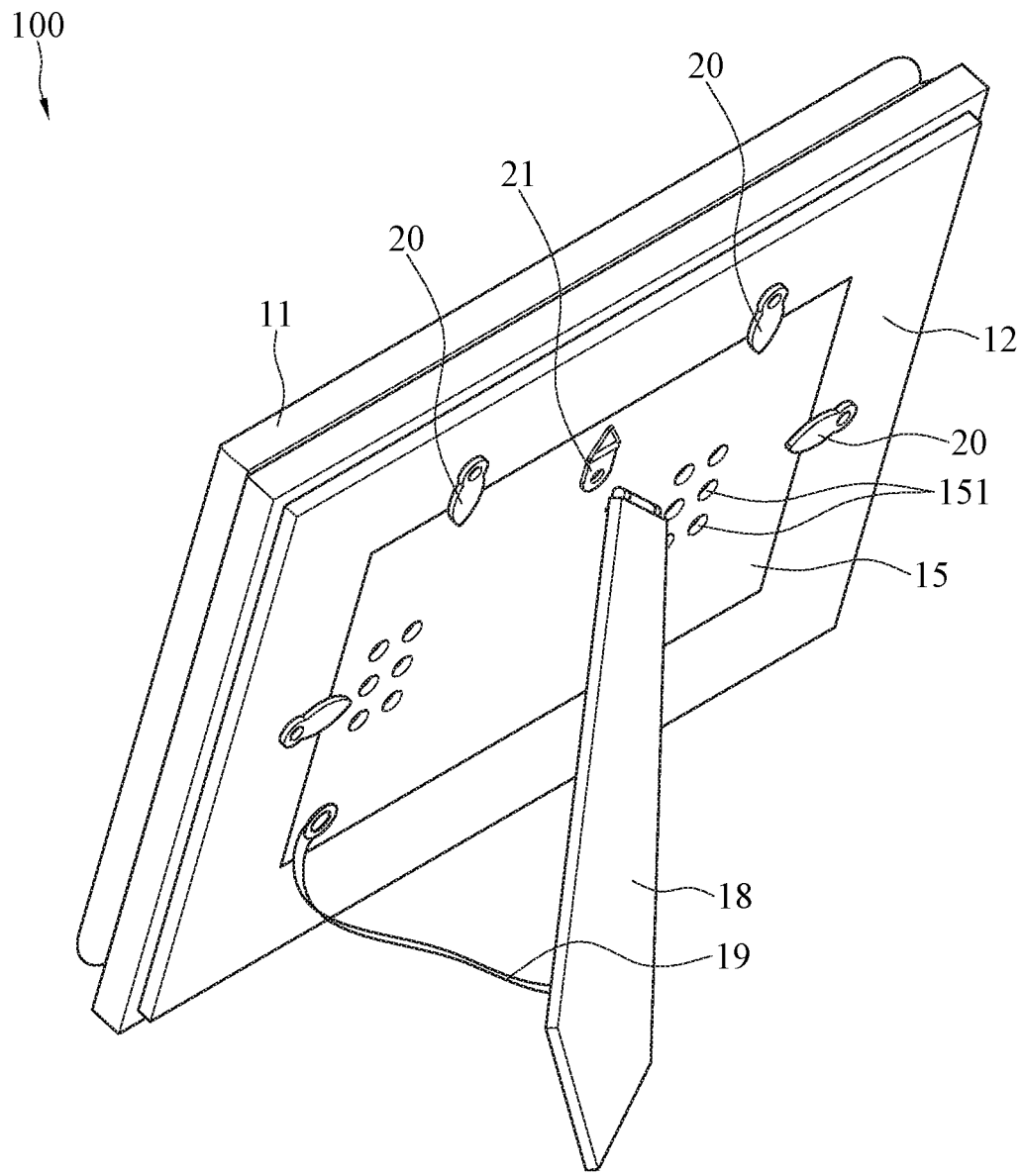
FIG. 6 illustrates a perspective view (2) of the scent frame of the third embodiment.

FIG. 4 illustrates a partial sectional view of the scent frame 100 of the third embodiment. When a photo 200 is received in the scent frame 100, the components and the photo 200 are arranged in an order of the transparent plate 13, the photo 200, the bottom layer 16, the scent layer 14, the breathable layer 17, and the rear cover 15, along a direction from the frame window 111 to the opening 121. Please refer to FIGS. 5 and 6, illustrating perspective views (1) and (2) of the scent frame 100 of the third embodiment. In FIGS. 5 and 6, the photo 200 is received in the scent frame 100, and the scent frame 100 is standing.

Figure 7:
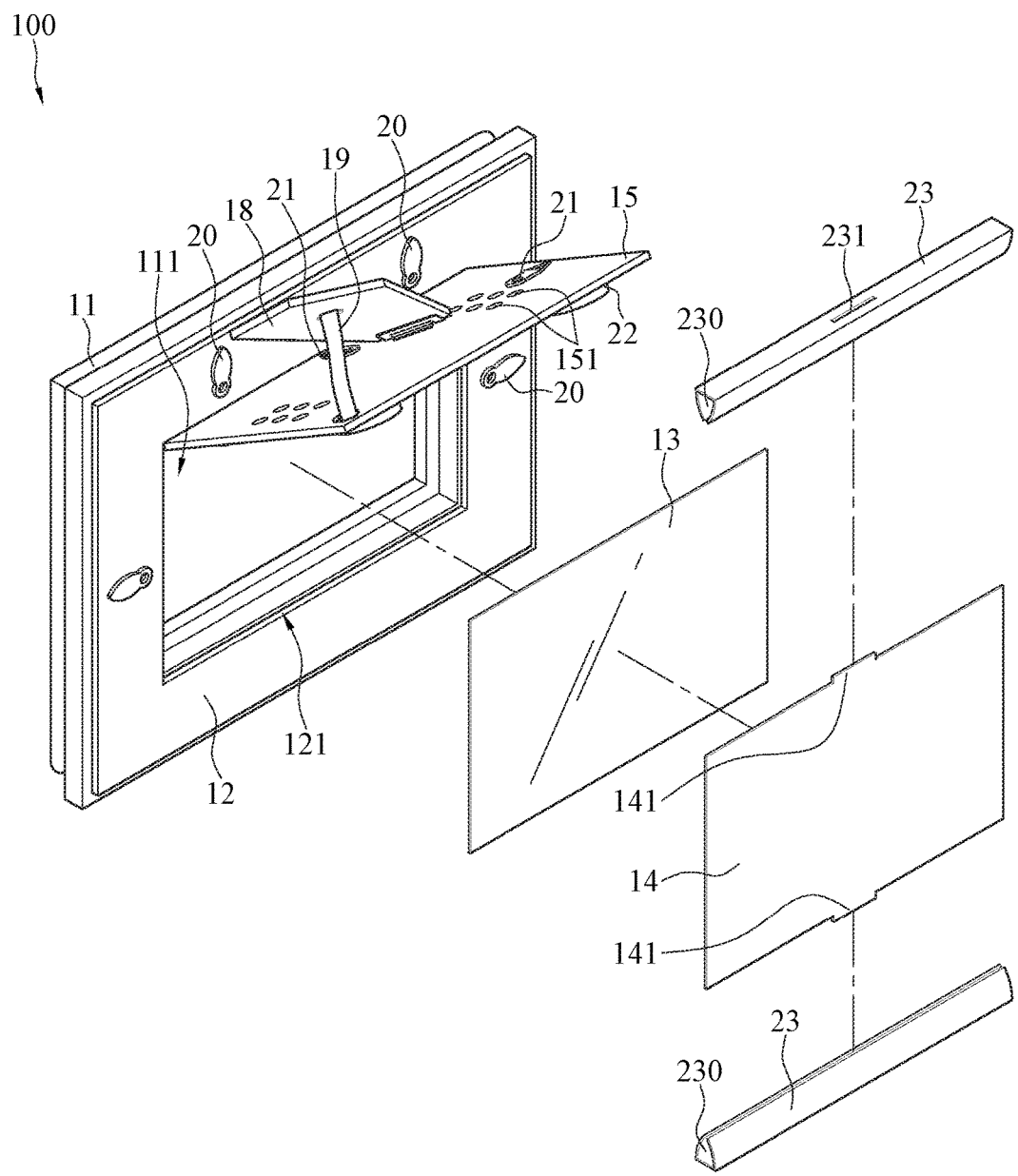
FIG. 7 illustrates an exploded view of a scent frame according to a fourth embodiment of the instant disclosure.

In one embodiment, as shown in FIG. 7, the scent frame 100 may further comprise two bars 23, and the scent layer 14 may further have two protruding portions 141 respectively protruding from two opposite sides of the scent layer 14. Each of the bars 23 has a cut groove 230 and an assembling hole 231 at a bottom of the cut groove 230. The cut grooves 230 respectively receive the two opposite sides of the scent layer 14, and each of the assembling holes 231 is engaged with the corresponding protruding portion 141. In this embodiment, the cross section of the bar 23 is approximately U shaped, but embodiments are not limited thereto. In addition, the arrangement direction of the bars 23 corresponds to the arrangement direction of the scent layer 14; in other words, the length direction of the bars 23 is parallel to the length direction of the scent layer 14. In this embodiment, the assembling hole 231 may be defined through the bars 23 or not. Accordingly, the scent layer 14 can be assembled with the bars 23 to be elevated upward and spaced from its neighboring layers or plates. Further, when the scent layer 14 is elevated, the fragrance from the scent layer 14 can have a sufficient convection volume within the receiving space 112.

In the foregoing embodiments, the dimension of the through hole 151 may be in the range from 0.3 to 0.8 cm. In one embodiment, the dimension of the through hole 151 may be 0.7 cm, but embodiments are not limited thereto. The dimension of the through hole 151 may be determined by the size of the scent frame 100.

In the foregoing embodiments, the frame body 11 has a depth between the frame window 111 and the opening 121, and the depth is not less than 1 cm.

Based on the foregoing embodiments, the scent frame can be produced in different sizes, for example, 4×6 cm$^2$, 5×7 cm$^2$ or 8×10 cm$^2$. The fragrance of the scent layer can be spread from the through hole of the rear cover, and the scent frame may further comprise the bottom layer and the breathable layer to improve the durability and applicability of the scent frame.

Figure 8:
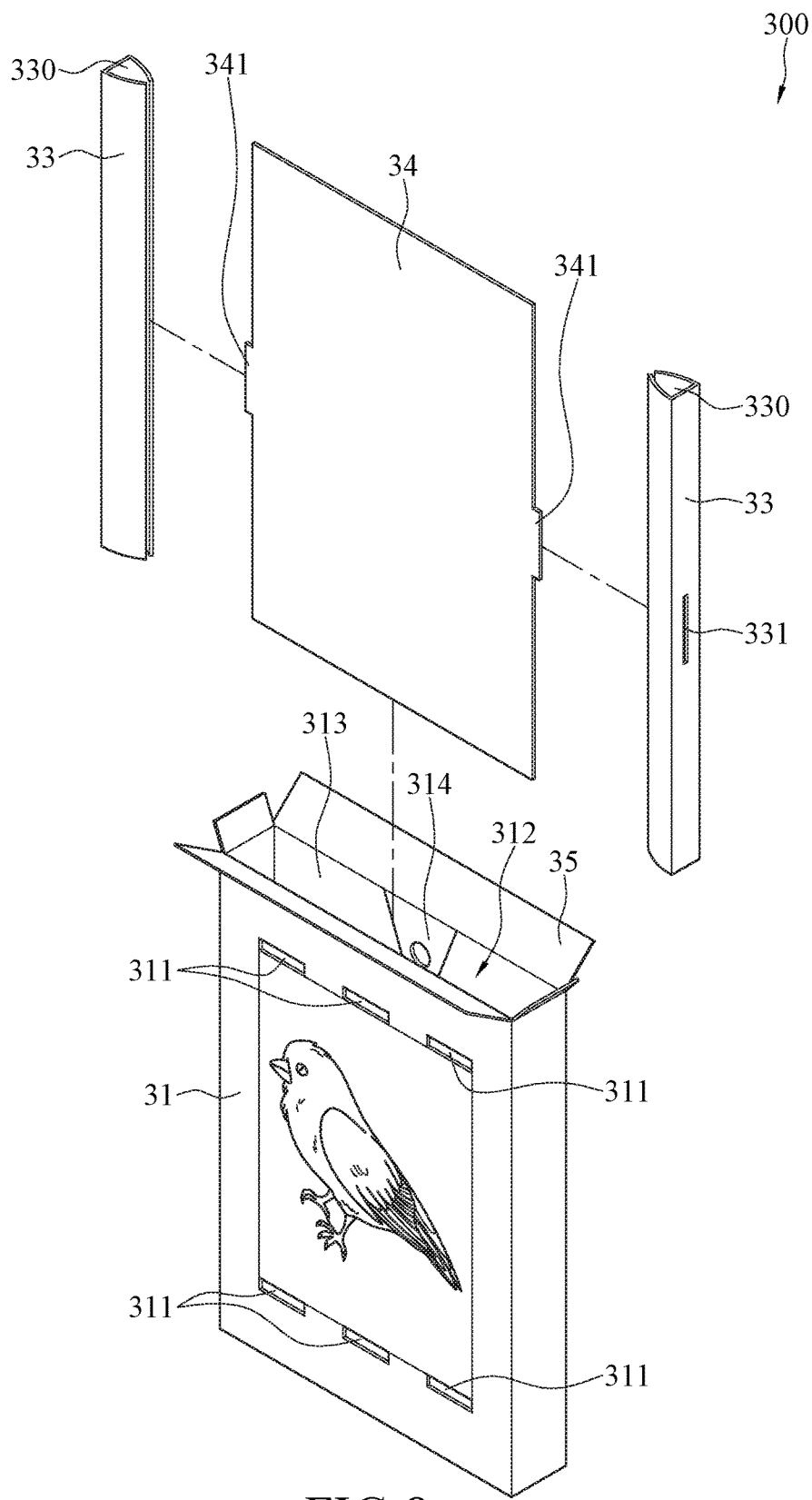
FIG. 8 illustrates an exploded view of a disposable scent paper box according to an exemplary embodiment of the instant disclosure.
Figure 9:
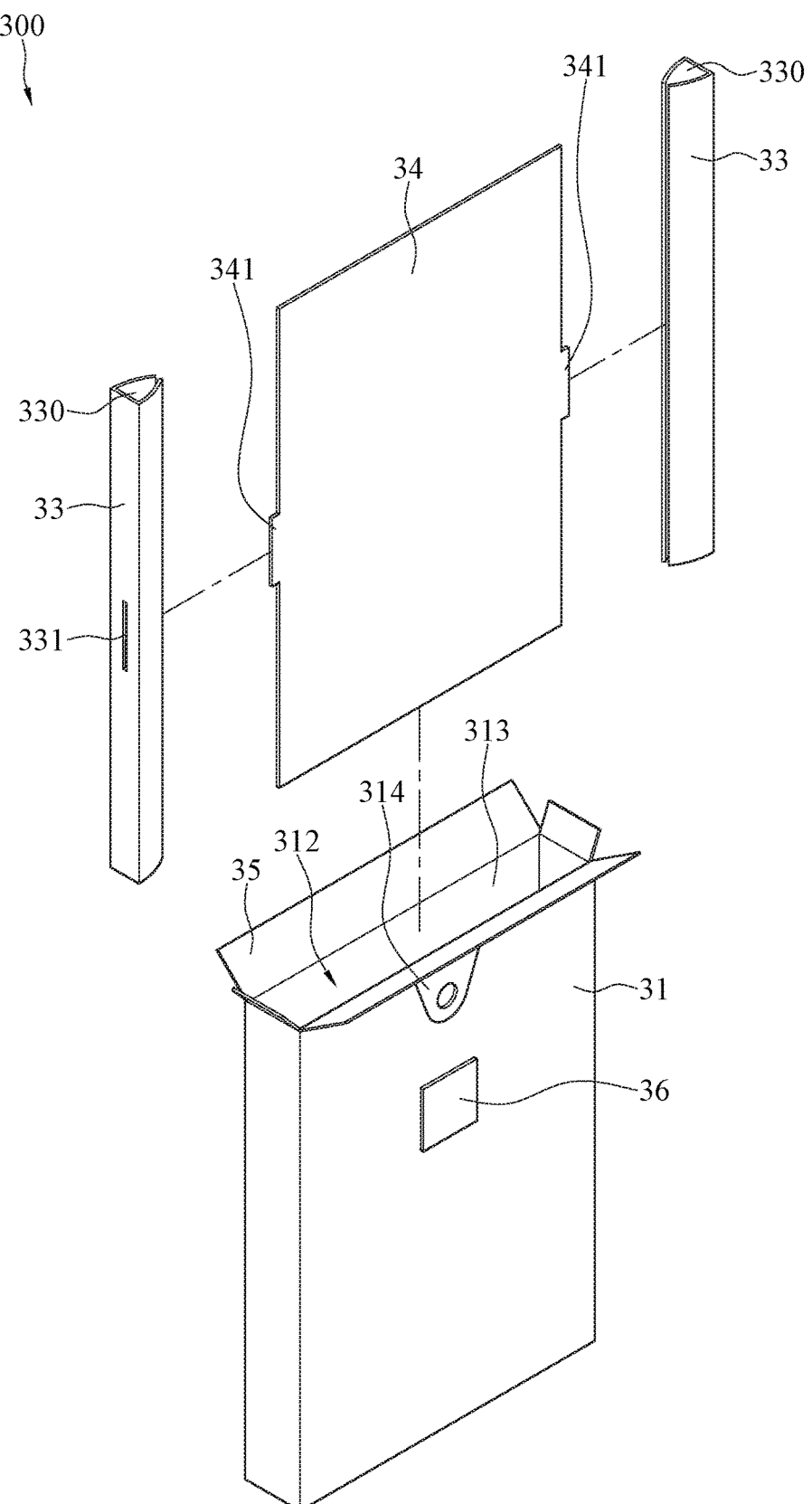
FIG. 9 illustrates another exploded view of the disposable scent paper box.

Please refer to FIGS. 8 and 9, illustrating a disposable scent paper box 300 according to an exemplary embodiment of the instant disclosure. The disposable scent paper box 300 comprises a box body 31, two bars 33, a scent layer 34, and a cover 35. The box body 31 comprises a receiving space 312 (i.e., the interior of the box body 31), a through hole 311, and an insertion opening 313, and the through hole 311 and the insertion opening 313 communicate with the receiving space 312. The scent layer 34 is received in the receiving space 312 and partially exposed from the through hole 311. The scent layer 34 has two protruding portions 341 respectively protruding from two opposite sides of the scent layer 34. The bars 33 are received in the receiving space 312. Each of the bars 33 has a cut groove 330 and an assembling hole 331 at the bottom of the cut groove 330. The cut grooves 330 receive the two opposite sides of the scent layer 34, and each of the assembling holes 331 is engaged with the corresponding protruding portion 341. In this embodiment, the box body 31 is of cuboid shape, but may be of other polygonal shapes. One surface of the box body 31 may have pictures or words for ornamental purposes, and the through hole 311 is configured on the surface of the box body 31 having ornamental pictures or words. In this embodiment, the number of the through hole 311 is six, and the shape of the through hole 311 is rectangular, but embodiments are not limited thereto. The shape and the number of the through hole 311 may be adjusted according to different needs. The through hole 311 is for spreading the fragrance of the scent layer 34 out of the receiving space 312. Because the scent layer 34 is engaged with the bars 33 and elevated upward, the scent layer 34 does not in contact with the inner wall of the box body 31 when being received in the box body 31. Hence, the durability of the product can increase. Further, when the scent layer 34 is elevated, the fragrance from the scent layer 34 can have a sufficient convection volume within the receiving space 312. In this embodiment, the insertion opening 313 and the cover 35 are at the upper side of the box body 31, and the box body 31 may have a hanging portion 314 for hanging the box body 31 on a wall. In addition, in one embodiment, an adhesive member 36 may be provided on a surface of the box body 31; specifically, the surface having the ornamental picture or words is different from the surface having the adhesive member 36. The adhesive member 36 is for sticking the box body 31 onto a surface or a wall.

Based on the embodiments of the scent frame and the disposable scent paper box, the fragrance from the scent layer can be spread over a room. In addition, the user can choose scent layers with different fragrance for different purposes, e.g., for delighting the user or for expelling parasites. The scent layer can be replaced conveniently or can be refilled with perfumes, fragrant essential oils, or flavorings for repeated use. The scent frame can be placed on a surface or hung on a wall, and the appearance of the scent frame is not changed when the scent layer is added to the scent frame. On the other hand, the disposable scent paper box not only can provide visually ornamental purposes for the user, but also can provide fragrance by the scent layer. The user can place or stick the disposable scent paper box on a surface (e.g., a desk surface or a wall surface).

While the instant disclosure has been described by the way of example and in terms of the preferred embodiments, it is to be understood that the invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. A scent frame, comprising:
a frame body, comprising a frame window;
a rear plate on one side of the frame body and fixedly connected to the frame body, wherein the rear plate comprises an opening;
a transparent plate in the frame body to shield the frame window, wherein a receiving space is formed between the transparent plate and the opening;
a scent layer in the receiving space and near to one surface of the transparent plate;
a rear cover on the opening of the rear plate to shield the receiving space, wherein the rear cover comprises at least one through hole;
a bottom layer in the receiving space and between the transparent plate and the scent layer; and
a breathable layer being a mesh structure and comprising a plurality of breathable holes, wherein the breathable layer is in the receiving space, and the bottom layer, the scent layer, and the breathable layer are sequentially stacked with each other.

2. The scent frame according to claim 1, wherein the rear cover is rotatably connected to a periphery of the opening.

3. The scent frame according to claim 1, further comprising a support, wherein one of two ends of the support is fixed on an outer surface of the rear cover, and the other end of the support is connected to the outer surface of the rear cover via a wire.

4. The scent frame according to claim 1, further comprising a plurality of pressing sheets on an outer surface of the rear plate, wherein the pressing sheets are on at least one side of the rear plate and near to the opening, and wherein when the pressing sheets are rotated relative to the rear plate, the pressing sheets are in contact with and positioned with the rear cover.

5. The scent frame according to claim 1, wherein a dimension of the at least one through hole is in the range from 0.3 to 0.8 cm.

6. The scent frame according to claim 1, wherein the rear cover further comprises at least one hanging member on an outer surface of the rear cover.

7. The scent frame according to claim 1, wherein the rear cover further comprises a plurality of cushion pads on an inner surface of the rear cover.

8. The scent frame according to claim 1, wherein a depth is between the frame window and the opening, and the depth is not less than 1 cm.

9. The scent frame according to claim 1, wherein the scent layer comprises a woven cloth layer.

10. The scent frame according to claim 1, wherein the scent layer comprises a paper-made layer.

11. The scent frame according to claim 1, wherein the scent layer comprises a foam layer.

12. A scent frame, comprising:
a frame body, comprising a frame window;
a rear plate on one side of the frame body and fixedly connected to the frame body, wherein the rear plate comprises an opening;
a transparent plate in the frame body to shield the frame window, wherein a receiving space is formed between the transparent plate and the opening;
a scent layer in the receiving space and near to one surface of the transparent plate;
a rear cover on the opening of the rear plate to shield the receiving space, wherein the rear cover comprises at least one through hole; and
two bars received in the receiving space, wherein the scent layer further comprises two protruding portions respectively protruding from two opposite sides of the scent layer, each of the bars has a cut groove and an assembling hole at a bottom of the cut groove, the cut grooves respectively receive the two opposite sides of the scent layer, each of the assembling holes is engaged with the corresponding protruding portion.

13. The scent frame according to claim 12, further comprising a support, wherein one of two ends of the support is fixed on an outer surface of the rear cover, and the other end of the support is connected to the outer surface of the rear cover via a wire.

14. The scent frame according to claim 12, further comprising a plurality of pressing sheets on an outer surface of the rear plate, wherein the pressing sheets are on at least one side of the rear plate and near to the opening, and wherein when the pressing sheets are rotated relative to the rear plate, the pressing sheets are in contact with and positioned with the rear cover.

15. The scent frame according to claim 12, wherein a dimension of the at least one through hole is in the range from 0.3 to 0.8 cm.

16. The scent frame according to claim 12, wherein the rear cover further comprises a plurality of cushion pads on an inner surface of the rear cover.

17. The scent frame according to claim 12, wherein a depth is between the frame window and the opening, and the depth is not less than 1 cm.

18. The scent frame according to claim 12, wherein the scent layer comprises a woven cloth layer.

19. The scent frame according to claim 12, wherein the scent layer comprises a paper-made layer.

20. The scent frame according to claim 12, wherein the scent layer comprises a foam layer.

* * * * *